(12) United States Patent
Bell et al.

(10) Patent No.: US 12,324,736 B2
(45) Date of Patent: *Jun. 10, 2025

(54) STENTED PROSTHETIC HEART VALVE WITH VARIABLE STIFFNESS AND METHODS OF USE

(71) Applicant: Medtronic Vascular Galway Unlimited Company, Ballybrit (IE)

(72) Inventors: Rodney Bell, Galway (IE); Declan Costello, Galway (IE)

(73) Assignee: MEDTRONIC VASCULAR GALWAY UNLIMITED COMPANY, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/368,541

(22) Filed: Sep. 14, 2023

(65) Prior Publication Data

US 2024/0000564 A1 Jan. 4, 2024

Related U.S. Application Data

(60) Continuation of application No. 17/845,222, filed on Jun. 21, 2022, now Pat. No. 11,857,413, which is a
(Continued)

(51) Int. Cl.
*A61F 2/24* (2006.01)
*A61F 2/86* (2013.01)
*A61F 2/91* (2013.01)

(52) U.S. Cl.
CPC .... *A61F 2/2418* (2013.01); *A61F 2250/0018* (2013.01); *A61F 2250/0029* (2013.01)

(58) Field of Classification Search
CPC ........ A61F 2/24; A61F 2/2409; A61F 2/2418; A61F 2250/0018; A61F 2250/0029;
(Continued)

(56) References Cited

U.S. PATENT DOCUMENTS

| 3,657,744 A | 4/1972 | Ersek | |
|---|---|---|---|
| 5,836,966 A * | 11/1998 | St. Germain | ........... A61F 2/915 606/198 |

(Continued)

FOREIGN PATENT DOCUMENTS

EP 1941848 7/2008

OTHER PUBLICATIONS

PCT/US2015/010754, The International Search Report and The Written Opinion of the International Searching Authority, mailed Apr. 8, 2015.
(Continued)

*Primary Examiner* — Seema Mathew
(74) *Attorney, Agent, or Firm* — Wentsler LLC

(57) ABSTRACT

A prosthetic heart valve including a stent frame and a valve structure. The valve structure is disposed within a lumen of the stent frame. The stent frame is configured to self-expand from a compressed condition for transluminal delivery. The stent frame has a lattice structure forming a tubular shape defining a circumference and a plurality of closed cells arranged to define a band exhibiting a variable radial stiffness. The prosthesis can be deployed such that the band applies a minimal force on to anatomical locations relating to the heart's conductive pathways. A region of the band otherwise having low radial stiffness is located at or over a conductive pathway upon final implant.

17 Claims, 8 Drawing Sheets

Related U.S. Application Data continuation of application No. 16/898,674, filed on Jun. 11, 2020, now Pat. No. 11,395,736, which is a division of application No. 15/665,998, filed on Aug. 1, 2017, now Pat. No. 10,736,738, which is a division of application No. 14/164,301, filed on Jan. 27, 2014, now Pat. No. 9,750,603.

(58) Field of Classification Search
CPC ............ A61F 2/915; A61F 2002/91558; A61F 2002/91575; A61F 2250/0036; A61F 2250/0039; A61F 2250/0098; A61F 2/86; A61F 2/91
See application file for complete search history.

(56) References Cited

U.S. PATENT DOCUMENTS

| | | | |
|---|---|---|---|
| 5,938,697 A * | 8/1999 | Killion | A61F 2/915 623/1.15 |
| 6,027,526 A | 2/2000 | Limon et al. | |
| 6,468,302 B2 * | 10/2002 | Cox | A61F 2/91 623/1.15 |
| 6,602,281 B1 | 8/2003 | Klein | |
| 6,613,074 B1 | 9/2003 | Mitelberg et al. | |
| 6,790,230 B2 | 9/2004 | Beyerdorf et al. | |
| 6,899,729 B1 * | 5/2005 | Cox | A61F 2/915 623/1.13 |
| 7,018,406 B2 | 3/2006 | Seguin | |
| 7,252,682 B2 | 8/2007 | Seguin | |
| 7,258,697 B1 * | 8/2007 | Cox | A61F 2/915 623/1.14 |
| 7,470,285 B2 | 12/2008 | Nugent et al. | |
| 7,637,937 B2 * | 12/2009 | Case | A61F 2/90 623/1.15 |
| 7,857,845 B2 | 12/2010 | Stacchino et al. | |
| 8,414,645 B2 * | 4/2013 | Dwork | A61F 2/2436 623/2.11 |
| 9,180,005 B1 | 11/2015 | Lashinski et al. | |
| 9,259,336 B2 | 2/2016 | Schaeffer et al. | |
| 9,750,603 B2 * | 9/2017 | Bell | A61F 2/2418 |
| 10,271,977 B2 * | 4/2019 | Longo | A61F 2/89 |
| 10,321,994 B2 | 6/2019 | Erzberger | |
| 10,441,447 B2 * | 10/2019 | Krieger | A61F 2/844 |
| 10,470,880 B2 | 11/2019 | Braido | |
| 10,857,413 B2 * | 12/2020 | Hetrick | A63B 21/4023 |
| 10,881,541 B1 * | 1/2021 | Rocha-Singh | A61B 8/065 |
| 11,090,153 B2 | 8/2021 | Haarer et al. | |
| 11,197,754 B2 | 12/2021 | Saffari et al. | |
| 2003/0135265 A1 | 7/2003 | Stinson | |
| 2004/0034402 A1 | 2/2004 | Bales | |
| 2004/0210304 A1 | 10/2004 | Seguin et al. | |
| 2004/0243216 A1 | 12/2004 | Gregorich et al. | |
| 2006/0100690 A1 | 5/2006 | Venturelli | |
| 2006/0122692 A1 | 6/2006 | Gilad | |
| 2006/0173531 A1 | 8/2006 | Richter | |
| 2006/0200227 A1 | 9/2006 | Jang | |
| 2006/0265056 A1 | 11/2006 | Nguyen | |
| 2008/0140189 A1 | 6/2008 | Nguyen | |
| 2008/0167707 A1 * | 7/2008 | Marrey | A61F 2/91 623/1.16 |
| 2009/0287296 A1 | 11/2009 | Manasse | |
| 2010/0094391 A1 * | 4/2010 | Heraty | A61F 2/91 623/1.11 |
| 2011/0022157 A1 | 1/2011 | Essinger et al. | |
| 2011/0098804 A1 * | 4/2011 | Yeung | A61F 2/2412 623/2.1 |
| 2011/0112626 A1 | 5/2011 | Van der Leest | |
| 2011/0251680 A1 | 10/2011 | Tran | |
| 2011/0264196 A1 | 10/2011 | Savage | |
| 2012/0071969 A1 | 3/2012 | Li | |
| 2012/0101572 A1 * | 4/2012 | Kovalsky | A61F 2/2418 623/2.19 |
| 2012/0116496 A1 | 5/2012 | Chuter | |
| 2012/0116498 A1 * | 5/2012 | Chuter | A61F 2/2412 623/1.26 |
| 2012/0123529 A1 | 5/2012 | Levi et al. | |
| 2012/0143316 A1 | 6/2012 | Seguin | |
| 2013/0178928 A1 * | 7/2013 | Vyas | A61F 2/915 623/1.16 |
| 2013/0261739 A1 | 10/2013 | Kuehn | |
| 2013/0282113 A1 * | 10/2013 | Punga | A61F 2/2418 623/2.17 |
| 2013/0338766 A1 | 12/2013 | Hastings et al. | |
| 2014/0000112 A1 | 1/2014 | Braido | |
| 2014/0025157 A1 | 1/2014 | Abunassar | |
| 2014/0107767 A1 | 4/2014 | Braido | |
| 2014/0114408 A1 | 4/2014 | Dwork | |
| 2014/0200660 A1 | 7/2014 | Savage et al. | |
| 2014/0214157 A1 | 7/2014 | Bortlein | |
| 2014/0277412 A1 | 9/2014 | Bortlein | |
| 2015/0209140 A1 | 7/2015 | Bell | |
| 2015/0265438 A1 | 9/2015 | Hossainy et al. | |
| 2015/0320556 A1 | 11/2015 | Levi et al. | |
| 2016/0015539 A1 | 1/2016 | Donovan et al. | |
| 2016/0106537 A1 | 4/2016 | Christianson et al. | |
| 2016/0120646 A1 | 5/2016 | Dwork | |
| 2016/0200035 A1 * | 7/2016 | Jacobs | A61L 31/14 264/80 |
| 2016/0270910 A1 | 9/2016 | Birmingham | |
| 2017/0325946 A1 | 11/2017 | Bell et al. | |
| 2019/0224008 A1 | 7/2019 | Bressloff | |
| 2019/0247209 A1 * | 8/2019 | Longo | A61F 2/915 |
| 2020/0297484 A1 | 9/2020 | Bell et al. | |
| 2020/0345498 A1 | 11/2020 | Poucher et al. | |
| 2021/0298896 A1 | 9/2021 | Pham et al. | |
| 2021/0386566 A1 | 12/2021 | Sreedharan et al. | |
| 2022/0054260 A1 | 2/2022 | Koop et al. | |
| 2022/0142777 A1 | 5/2022 | Scheinblum et al. | |
| 2022/0401207 A1 | 12/2022 | Zavattieri et al. | |
| 2023/0063142 A1 | 3/2023 | O'Connor et al. | |

OTHER PUBLICATIONS

CN Application No. 201580005926.2, 1$^{st}$ Office Action, mailed May 11, 2017, 16pgs.

Till, J.A. et al., "Histopathological findings in three children with His bundle tachycardia occurring subsequent to cardiac surgery," European Heart Journal, 13, pp. 709-712 (1992).

Van der Boon, Robert M. et al., "New conduction abnormalities after TAVI-frequency and causes," Nature Reviews Cardiology, vol. 9, pp. 454-463 (Aug. 2012).

Aktug, Omer et al., "Incidence and predictors of left bundle branch block after transcatheter aortic valve implantation," Int J Cardiol, pp. 1-5 (2012).

Piazza, Nicolo et al., "Persistent conduction abnormalities and requirements for pacemaking six months after transcatheter aortic valve implantation," EuroIntervention, pp. 475-484 (2010).

Rubin, Joes M. et al. "Atrioventricular Conduction Disturbance Characterization in Transcatheter Aortic Valve Implantation with the CoreValve Prosthesis," Circ Cardiovasc Interv, pp. 280-286 (2011).

Nuis, Rutger-Jan et al., "Timing and potential mechanisms of new conduction abnormalities during the implantation of the Medtronic CoreValve System in patients with aortic stenosis," European Heart Journal, pp. 1-8 (2011).

Nuis, RJ et al., "Timing and Potential Mechanisms of New Conduction Abnormalities During the Implantation of a Medtronic CoreValve System in Patients with Aortic Stenosis," Euro PCR, pp. 1-39 (2011).

Grube, Eberhard et al., "Feasibility of Transcatheter Aortic Valve Implantation Without Balloon Pre-Dilation: A Pilot Study," JACC Cardiovascular Intervention, vol. 4, No. 7, pp. 751-757 (2011).

Schroeter, Thomas et al., "Predictors of permanent pacemaker implantation after Medtronic CoreValve bioprosthesis implantation," European Society of Cardiology, pp. 1-5 (2012).

van der Boon, Robert M.A. et al., "Pacemaker dependency after transcatheter aortic valve implantation with the self-expanding

(56) References Cited

OTHER PUBLICATIONS

Medtronic CoreValve System," International Journal of Cardiology, pp. 1-5, (2013) <http://dx.doi.org/10.1016/j.ijcard.2012.11.115>.

Piazza, Nicole et al., "Anatomy of the Aortic Valvar Complex and Its Implications for Transcatheter Implantation of the Aortic Valve," Circulation Cardiovascular Interventions, Journal of the American Heart Association, 1, pp. 74-81 (2008).

Kim, Won-Jang, "Can we Prevent AV Block after CoreValve Implantation?" University of Ulsan College of Medicine, ASAN Medical Center, Cardio Vascular Research Foundation, Presentation given at TCT AP, pp. 1-45 (2013).

Binder, Ronald K. et al., "Impact of Post-Implant SAPIEN XT Geometry and Position on Conduction Disturbances, Hemodynamic Performance, and Paravalvular Regurgitation," JACC Cardiovascular Interventions, vol. 6, No. 5, pp. 462-468 (2013).

Modine, T., "Conduction abnormalities and TAVI: What do we need to know," Centre Hospitalier Regional, Universitaire de Lille, pp. 1-36 (Feb. 2013).

Petronio, A.S., "Case Report Session, Cardiac Disturbances Prevention," University of Pisa, pp. 1-30 (Feb. 27, 2013).

Roten, Laurent et al., "Atrioventricular Conduction After Transcatheter Aortic Valve Implantation and Surgical Aortic Valve Replacement," Journal of Cardiovascular Electrophysiology, pp. 1-8 (Apr. 2, 2012).

Biner, Simon et al., "Hemodynamic Impact and Outcome of Permanent Pacemaker Implantation Following Transcatheter Aortic Valve Implantation," The American Journal of Cardiology, pp. 1-6 (2013).

Buellesfeld, Lutz, et al., "Impact of Permanent Pacemaker Implantation on Clinical Outcome Among Patients Undergoing Transcatheter Aortic Valve Implantation," Journal of the American College of Cardiology, pp. 1-9 (2012).

Cheong, Dr. Adrian, "Implantation depth and conduction disturbances using the self-expanding TAVI prosthesis," Prince of Wales Hospital, The Chinese University of Hong Kong, pp. 1-31 (2013).

Houthuizen, Patrick et al., "Left Bundle Branch Blocked Inducted by Transcatheter Aortic Valve Implantation Increases Risk of Death," Circulation, Journal of the American Heart Association, pp. 1-28 (Jul. 12, 2012).

Staubach, Stephen et al., "Original Studies. Impact of Aortic Valve Calcification on the Outcome of Transcatheter Aortic Valve Implantation: Results from the Prospective Multicenter German TAVI Registry," Wiley Periodicals, Inc., Catheterization and Cardiovascular Interventions pp. 1-8 (2012).

Hoffmann, Rainer et al., "Impact of a New Conduction Defect After Transcatheter Aortic Valve Implantation on Left Ventricular Function," JACC: Cardiovascular Interventions, by the American College of Cardiology Foundation, vol. 5, No. 12, pp. 1258-1263 (Dec. 2012).

Igawa, Osamu et al., "OE-328, The Useful Anatomical Information for Catheter Ablation Concerning the Relationship between the Aortic Non-coronary Cusp and the His Bundle," Circulation Journal, vol. 73, Suppl. I, pp. 257 (2009).

Dodge-Khatami, A. et al., "Impact of junctional ectopic tachycardia on postoperative morbidity following repair of congenital heart defects," European Journal of Cardio-thoracic Surgery, vol. 21, pp. 255-259 (2002).

Muller, David et al., "Impact of New Left Bundle Branch Block or Pacemaker Implantation on Outcomes Following Transcatheter Aortic Vavle Implantation in the CoreValve Australia New Zealand Study," Euro PCR, pp. 1-18 (2013).

Neragi-Miandoab, Siyamek, et al., "Review Article, A Review of Most Relevant Complications of Transcatheter Aortic Valve Implantation," Hindawi Publishing Corporation, vol. 2013, pp. 1-13 (2013).

Piazza, Nicolo et al., "Early and Persistent Intraventricular Conduction Abnormalities and Requirements for Pacemaking After Percutaneous Replacement of the Aortic Valve," JACC: Cardiovascular Interventions, The American College of Cardiology Foundation, vol. 1, No. 3, pp. 310-316 (2008).

Roten, Laurent et al., "Incidence and Predictors of Atrioventricular Conduction Impairment and Need for Permanent Pacemaker After Transcatheter Aortic Valve Implantation," Inselspital, Bern University Hospital, Switzerland, pp. 1 (2011).

Saji, Mike et al., "Autopsy finding of the Sapien XT valve from a patient who died suddenly after transcatheter aortic valve replacement," Japanese Associate of Cardiovascular Intervention and Therapeutics, pp. 1-5 (Jan. 1, 2013).

Testa, Luca et al., "Clinical Impact of Persistent Left Bundle Branch Block after Transcatheter Aortic Valve Implantation with CoreValue Revalving System," Circulation, Journal of the American Heart Association, pp. 1-27 (2013).

Toggweiler, Stefan et al., "Challenges in transcatheter aortic valve implantation," Swiss Medical Weekly, The European Journal of Medical Sciences, pp. 1-15 (2012).

Wenaweser, Peter et al., "Impact of Conduction Disturbances Post Transcatheter Aortic Valve Implantation in Real World Patients: One Year Outcomes, the Advance Study," Euro PCR, pp. 1-18 (2013).

Wolff, Rafael et al., "Low rate of conduction disturbances and the need of permanent pacemaker after transcatheter aortic valve implantation with the core-value bioprosthesis," Sunnybrook Health Sciences Centre, pp. 1-15 (2013).

* cited by examiner

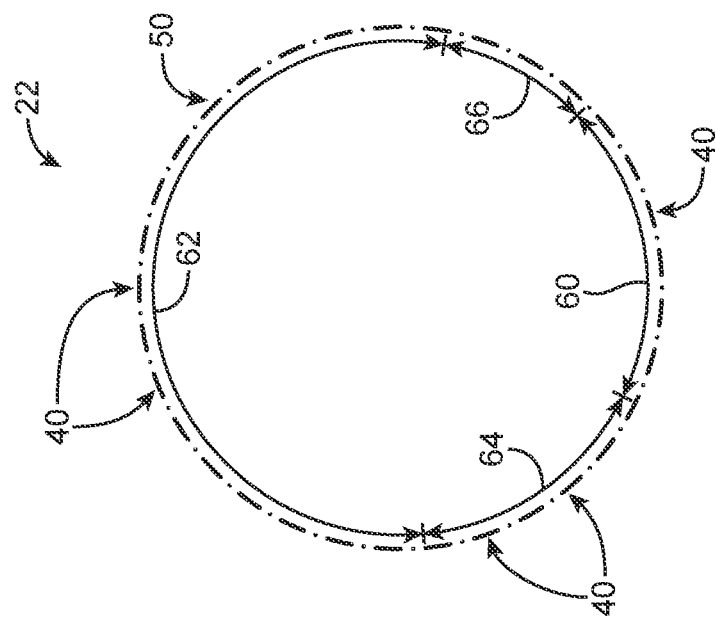
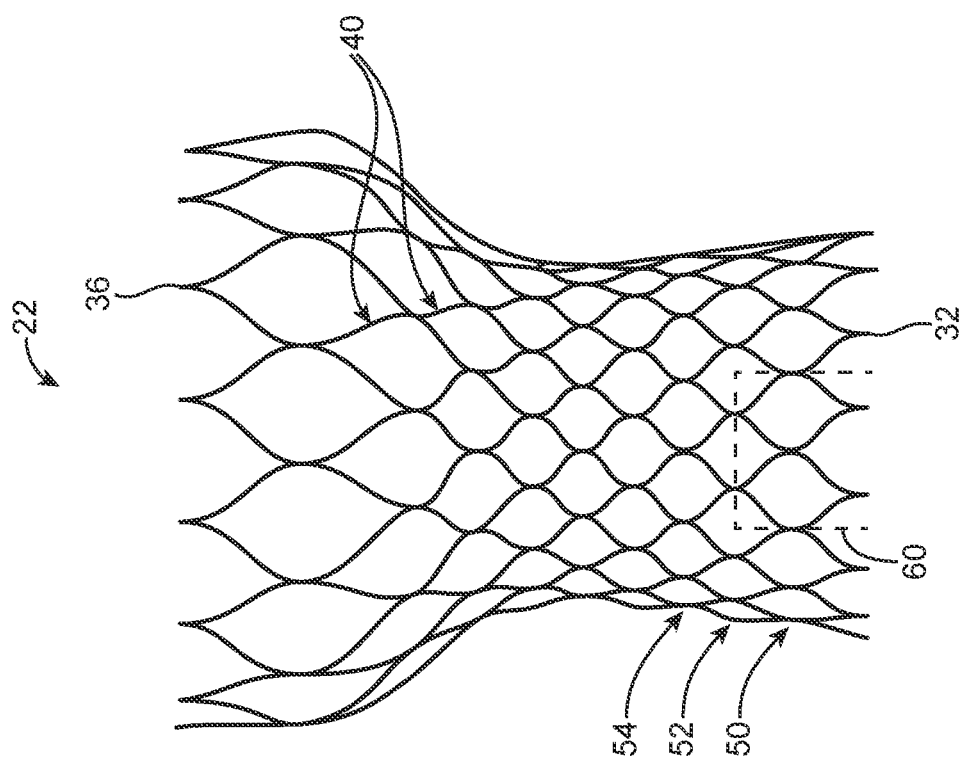
FIG. 2B
FIG. 2A

STENTED PROSTHETIC HEART VALVE WITH VARIABLE STIFFNESS AND METHODS OF USE

RELATED APPLICATIONS

This application is a continuation of U.S. application Ser. No. 17/845,222, filed Jun. 21, 2022, which is a continuation of U.S. application Ser. No. 16/898,674 filed Jun. 11, 2020, now U.S. Pat. No. 11,395,736, which is a divisional of U.S. application Ser. No. 15/665,998 filed Aug. 1, 2017, now U.S. Pat. No. 10,736,738, which is a divisional of U.S. application Ser. No. 14/164,301 filed Jan. 27, 2014, now U.S. Pat. No. 9,750,603, the entire contents of each application which are incorporated herein by reference.

BACKGROUND

The present disclosure relates to prosthetic heart valves. More particularly, it relates to stented prosthetic heart valves and related methods of use.

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open-heart surgery inflicts significant patient trauma and discomfort, and exposes the patient to a number of potential risks.

More recently, minimally invasive systems and techniques have been developed to facilitate catheter-based implantation of the valve prosthesis in the beating heart, intending to obviate the need for the use of classical sternotomy and cardiopulmonary bypass. With transcatheter (or transluminal) techniques, a valve prosthesis is compacted for delivery in a catheter and then advanced to the heart, for example through an opening in the femoral artery, subclavian artery, aorta, or ventricular apex to access the aortic valve. The delivered prosthesis is then deployed in the annulus of the valve to be replaced.

The heart valve prosthesis employed with transcatheter procedures generally includes an expandable, multiple-level frame or stent that supports a valve body having two or more leaflets. The actual shape and configuration of any particular prosthetic heart valve is dependent to some extent upon the native shape and size of the valve being repaired (i.e., aortic valve, mitral valve, tricuspid valve, or pulmonary valve). In general, prosthetic heart valve designs attempt to replicate the functions of the valve being replaced, and the stent utilized with the prosthesis dictates the final size and shape. In addition, the stent serves to anchor the transcatheter valve prosthesis at or about the native annulus.

One type of transcatheter valve stent frame can be initially provided in an expanded or uncrimped condition, then crimped or compressed about a balloon portion of a catheter. The balloon is subsequently inflated to expand and deploy the prosthetic heart valve. With other stented prosthetic heart valve designs, the stent frame is formed to be self-expanding. With these systems, the valve stent is crimped down to a desired size and held in that compressed state within a sheath for transluminal delivery. Retracting the sheath from this valve stent allows the stent to self-expand to a larger diameter, fixating at the native valve site. With either of these types of percutaneous stented prosthetic heart valve delivery devices, conventional sewing of the prosthetic heart valve to the patient's native tissue is typically not necessary.

In order to achieve necessary, long term anchoring at the native valve site, the stent frame must provide and maintain an elevated hoop strength and resistance to radially collapsing or compressive forces. A prosthetic valve that is not adequately anchored in place to resist the forces of the constantly changing vessel wall diameter, and turbulent blood flow there through, may dislodge itself, or otherwise become ineffective. In light of these requirements, transcatheter prosthetic heart valve stent frame designs are premised upon structural robustness, sufficient radial hoop strength or stiffness, and high fatigue strength. Further, the size or length of the stent is desirably selected to ensure elevated interface with the native anatomy. Lattice-type stent frame designs have been found to be well suited to meet these requirements, and are conventionally formatted to have a repeating pattern of closely sized, shaped and arranged cells. It has been found, however, that the stented transcatheter prosthetic heart valve may contribute to cardiac pacing issues post implantation.

For example, it is estimated that approximately 10-30% of self-expanding transcatheter aortic valve procedures require pacemaker implantation.

In light of the above, a need exists for a stented transcatheter prosthetic heart valve with reduced impact on the conductive pathways of the heart.

SUMMARY

Some aspects of the present disclosure relate to a prosthetic heart valve including a stent frame and a valve structure. The valve structure is disposed within a lumen of the stent frame. The stent frame is configured to self-expand from a compressed condition for transluminal delivery to a natural, expanded condition. The stent frame has a lattice structure forming a tubular shape defining a circumference. The lattice structure provides a plurality of closed cells arranged to define a band of closed cells extending about an entirety of the circumference, with the closed cells of the first band being equidistantly spaced from one another along the circumference. Further, the band is configured to have or exhibit a varying radial stiffness along the circumference in the natural condition. With this construction, the prosthetic heart valve can be deployed relative to the native anatomy such that the band applies a minimal force on to anatomical location(s) relating to the heart's conductive pathways. More particularly, a region of the band otherwise having or exhibiting low radial stiffness is located at or over a conductive pathway (e.g., conduction fibers of the left ventricular septum, SA node, Bundle of HIS, etc.), with the low radial stiffness region thus exerting a reduced force on the conductive pathway (as compared to the force exerted by other regions of the stent having a "normal" or elevated radial stiffness). Each of the closed cells includes a plurality of interconnected struts. In some embodiments, a dimension of at least one of the struts of the closed cells of the low radial stiffness region is less than a corresponding dimension of a corresponding strut of the closed cells of other regions of the band. In yet other embodiments, the band further includes a node body connecting two struts of each of the closed cells to one another, and a dimension of at least one of the node bodies of the low radial stiffness region is less than a corresponding dimension of each of the node bodies of other regions of the band.

Other aspects in accordance with principles of the present disclosure relate to a prosthetic heart valve having a stent frame and a valve structure. The valve structure is disposed within a lumen of the stent frame. The stent frame is configured to self-expand from a compressed condition for transluminal delivery to a natural, expanded condition. The stent frame has a lattice structure forming a tubular shape defining a circumference. The lattice structure provides a plurality of closed cells arranged to define first and second bands of closed cells each extending about an entirety of the circumference. The first band is located immediately longitudinally adjacent to the second band. In this regard, the first band is configured to have a varying radial stiffness along the circumference in the natural condition, and each of the closed cells of the second band are directly connected to a corresponding one of the closed cells of the first band. With this construction, the varying radial stiffness of the first band includes one or more regions of reduced radial stiffness that can be aligned with conductive pathways or tissue of the native valve anatomy.

Yet other aspects in accordance with principles of the present disclosure relate to a method of treating a native heart valve of a patient. The method includes delivering a prosthetic heart valve to the native heart valve. The prosthetic heart valve includes a stent frame maintaining a valve structure. The stent frame is configured to self-expand from a compressed condition to a natural, expanded condition. The stent frame has a lattice structure defining at least a first band of closed cells extending about an entirety of a circumference of the stent frame. The first band defines first and second regions, with the first region having a radial stiffness less than a radial stiffness of the second region. In this regard, the step of delivering the prosthetic heart valve includes maintaining the stent frame in the compressed condition within a delivery device. The prosthetic heart valve is then deployed from the delivery device into the native heart valve, including the stent frame self-expanding toward the natural condition. The first region (of reduced radial stiffness) is aligned with a desired anatomical location of the native heart valve. In some embodiments, the native heart valve is an aortic valve, and the desired anatomical location is along the left ventricular septum. In other embodiments, the desired anatomical location is a bundle of conduction fibers along the left ventricular septum.

BRIEF DESCRIPTION OF THE DRAWINGS

FIG. 2A is an enlarged side view of a stent frame portion of the prosthetic heart valve of FIG. 1A:

FIG. 2B is a simplified schematic end view of the stent frame of FIG. 2A;

DETAILED DESCRIPTION

As referred to herein, stented transcatheter prosthetic heart valve can assume a wide variety of different configurations, such as a bioprosthetic heart valve having tissue leaflets or a synthetic heart valve having polymeric, metallic or tissue-engineered leaflets, and can be specifically configured for replacing any of the four valves of the human heart. In general terms, the stented prosthetic heart valves of the present disclosure include a stent or stent frame maintaining a valve structure (tissue or synthetic), with the stent having a normal, expanded condition or arrangement and collapsible to a compressed condition or arrangement for loading within a delivery device. The stent frame is normally constructed to self-deploy or self-expand when released from the delivery device. For example, stents or stent frames are support structures that comprise a number of struts or wire segments arranged relative to each other to provide a desired compressibility and strength to the prosthetic heart valve. The struts or wire segments are arranged such that they are capable of self-transitioning from a compressed or collapsed condition to a normal, radially expanded condition. The struts or wire segments can be formed from a shape memory material, such as a nickel titanium alloy (e.g., Nitinol™). The stent frame can be laser-cut from a single piece of material, or can be assembled from a number of discrete components.

Figure 1A:
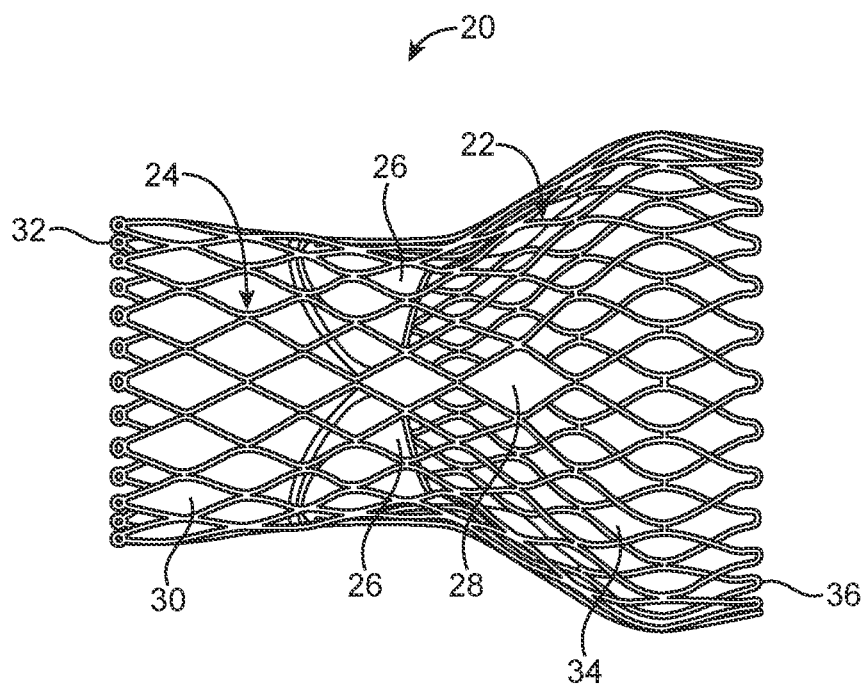
FIG. 1A is a side view of a stented prosthetic heart valve in accordance principles of the present disclosure and in a normal, expanded condition.
Figure 1B:
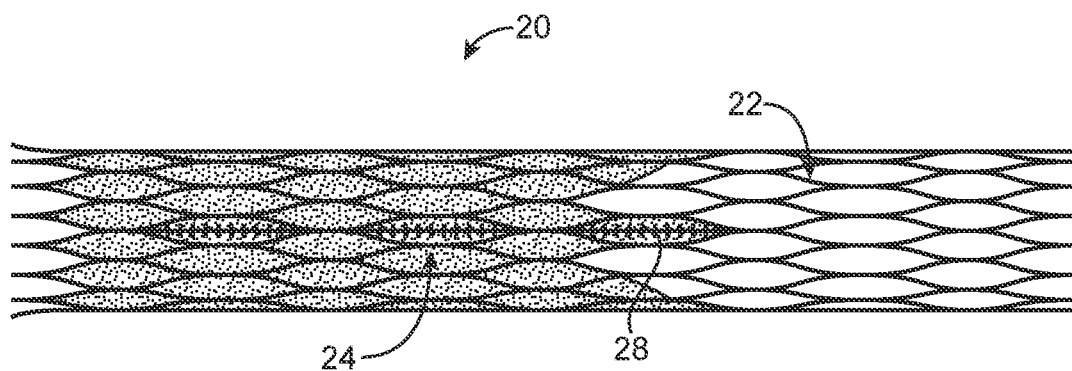
FIG. 1B is a side view of the prosthetic heart valve of FIGS. 1A and 1n a compressed condition.

With the above understanding in mind, one simplified, non-limiting example of a stented prosthetic heart valve 20 in accordance with principles of the present disclosure is illustrated in FIG. 1A. As a point of reference, the prosthetic heart valve 20 is shown in a normal or expanded condition in the view of FIG. 1A; FIG. 1B illustrates the prosthetic heart valve 20 in a compressed condition (e.g., when compressively retained within an outer catheter or sheath). The prosthetic heart valve 20 includes a stent or stent frame 22 and a valve structure 24. The stent frame 22 can generally assume any of the forms mentioned above, and is generally constructed so as to be self-expandable from the compressed condition (FIG. 1B) to the normal, expanded condition (FIG. 1A). In other embodiments, the stent frame 22 can be configured for expansion from the compressed condition to the expanded condition via operation of a separate tool, such as a balloon (i.e., the stent frame 22 can be a balloon-expandable stent frame as known in the art).

The valve structure 24 can assume a variety of forms, and can be, for example, formed from one or more biocompatible synthetic materials, synthetic polymers, autograft tissue, homograft tissue, xenograft tissue, or one or more other suitable materials. In some embodiments, the valve structure 24 can be formed, for example, from bovine, porcine, equine, ovine and/or other suitable animal tissues. In some embodiments, the valve structure 24 can be formed, for example, from heart valve tissue, pericardium and/or other suitable tissue. In some embodiments, the valve structure 24 can include or form one or more leaflets 26. For example, the valve structure 24 can be in the form of a tri-leaflet bovine pericardium valve, a bi-leaflet valve, or other suitable valve. In some constructions, the valve structure 24 can comprise two or three leaflets that are fastened together at enlarged lateral end regions to form commissural points 28, with the unattached edges forming cooptation edges of the valve structure 24. The leaflets 26 can be fastened to a skirt (not shown) that in turn is attached to the stent frame 22. The upper ends of the commissural points 28 can define an inflow portion 30 corresponding to a first or inflow end 32 of the prosthesis 20. The opposite end of the valve structure 24 can define an outflow portion 34 corresponding to a second or outflow end 36 of the prosthesis 20.

With the exemplary construction of FIGS. 1A and 1B, the prosthetic heart valve 20 can be configured (e.g., sized and shaped) for replacing or repairing an aortic valve. Alternatively, other shapes are envisioned, adapted to mimic the specific anatomy of the valve to be repaired (e.g., the stented prosthetic heart valve of the present disclosure can alternatively be shaped and/or sized for replacing a native mitral, pulmonic, or tricuspid valve).

The self-expanding stent frame 22 is configured to generate a high radially expansive force (alternatively referred to as a chronic outward force) when forced to the compressed condition of FIG. 1B for self-deployment, and exhibit high resistance to radial compression (alternatively referred to as a radial resistive force or force required to compress the stent frame 22) once in the normal, expanded condition of FIG. 1A. It will be recognized that when implanted, the stent frame 22 will expand from the compressed condition toward the normal condition; however, the stent frame 22 will not fully attain the normal condition. Instead, the stent frame 22 is sized and shaped in accordance with the expected anatomy such that the stent frame 22 intimately contacts the native anatomy at a level of expansion less than the normal condition. In this way, the chronic outward force attribute of the stent frame 22 ensures that the stent frame 22 securely lodges or anchors against the native anatomy, with the stent frame 22 thus applying a force onto the native anatomy. This inherent characteristic of the stent frame 22 can also be referred to in terms of radial stiffness.

With this in mind, FIG. 2A illustrates the stent frame 22 in isolation. The stent frame 22 has a lattice structure that provides a plurality of closed cells 40 (several of which are referenced in FIG. 2A). The lattice structure collectively forms a tubular shape defining a circumference (best reflected by the schematic end view of FIG. 2B). The closed cells 40 are arranged about the circumference, and the lattice structure can be viewed as defining one or more circumferential bands of closed cells. For example, first, second and third circumferential bands 50-54 are identified in FIG. 2A. The stent frame 22 is configured such that a radial stiffness exhibited along the first band 50 (in at least the normal, expanded condition) varies along the circumference as described below. The radial stiffness exhibited along the second and third bands 52, 54 can be substantially uniform along an entirety of the circumference in some embodiments; alternatively, more than one circumferential band defined by the lattice structure of stent frame 22 have a varying radial stiffness along the circumference (e.g., the first and second bands 50, 52 can have the varying radial stiffness attributes described below). Regardless, the variable radial stiffness embodied by at least the first circumferential band 50 is configured to impart minimal or reduced force on contacted tissue upon implant of the stent frame 22, for example imparting less chronic outward force onto a native conduction fibers or bundle.

The variable radial stiffness of the first band 50 can be characterized by regions of differing radial stiffness. For example, in the view of FIG. 2B, a first region 60 and a second region 62 are identified. As a point of reference. FIG. 2B is a schematic end view of the stent frame 22 from the inflow end 32, illustrating the tubular nature of the stent frame 22 in the normal, expanded state, and generally reflects a location of the closed cells 40 along the first band 50. With this in mind, each of the regions 60, 62 consists of at least two circumferentially adjacent closed cells 40. The stent frame 22 is constructed such that the radial stiffness along the first region 60 is less than the radial stiffness along the second region 62. In this regard, the stent frame 22 can exhibit a constant radial stiffness along an entirety of the first region 60 or along an entirety of the second region 62, or the radial stiffness within the regions 60/62 can vary slightly, respectively. Regardless, the minimum radial stiffness at any location along the second region 62 is greater than the maximum radial stiffness along any portion of the first region 60. The elevated radial stiffness of the second region 62 (as compared to the radial stiffness of first region 60) is akin to that provided at other longitudinal locations along the stent frame 22 and is conventionally sufficient for anchoring the stent frame 22 at a native valve site. A maximum radial stiffness along the first region 60 is sufficiently less than the radial stiffness along the second region 62 by a level sufficient to not induce conditions on to native tissue that would otherwise contribute to a need for a pacemaker. For example, a maximum radial stiffness along the first region 60 can be at least 10% less, alternatively at least 20% less, alternatively at least 40% less, alternatively at least 60% less than a minimum radial stiffness along the second region 62.

As reflected by FIG. 2B, an arc angle of the second region 62 is greater than that of the first region 60, with the second region 62 serving to promote robust anchoring of the stent frame 22 to the native valve anatomy (along the first band 50). Thus, at least a majority of the closed cells 40 of the first band 50 are along the second region 62. By way of one non-limiting example, with embodiments in which the first band 50 includes eighteen of the closed cells 40, the second region 62 consists of at least ten, optionally at least twelve of the closed cells 40. Conversely, the first region 60 includes no more than four of the closed cells 40, alternatively two of the closed cells 40.

In some embodiments, the first band 50 can be further viewed as providing third and fourth regions 64, 66 as identified in FIG. 2B. The third and fourth regions 64, 66 represent transitions in radial stiffness from the elevated radial stiffness second region 62 to the low radial stiffness first region 60. The transition regions 64, 66 thus exhibit a radial stiffness less than that of the second region 62 but greater than that of the first region 60, and encompass a relatively small arc length or arc angle (as compared to the arc length or arc angle of the second region 62). By way of one non-limiting example, the transition regions 64, 66 can each consist of no more than four, alternatively two, of the closed cells 40. The transition regions 64, 66 minimize the possibility that the stent frame 22 will buckle or in-fold at the first region 60.

The low radial stiffness first region 60 can be generated in a variety of fashions. In more general terms, the closed cells 40 of the variable radial stiffness first band 50 are generally akin to, and follow the pattern of, other bands defined by the stent frame 22. Thus, the closed cells 40 of the variable radial stiffness first band 50 are uniformly and equidistantly spaced from one another along the circumference. That is to say, the low radial stiffness first region 60 does not omit a portion or entirety of any of the closed cells 40. In other embodiments, the variable radial stiffness first band 50 includes the same number of closed cells 40 as the immediately longitudinally adjacent second band 52, with each of the closed cells 40 of the second band 52 being directly physically connected to a corresponding closed cell 40 of the first band 50. By maintaining the closed cell pattern along an entirety of the circumference of the first band 50, the first band 50 will have minimal negative impact, if any, on an overall fatigue strength of the stent frame 22.

Figure 3:
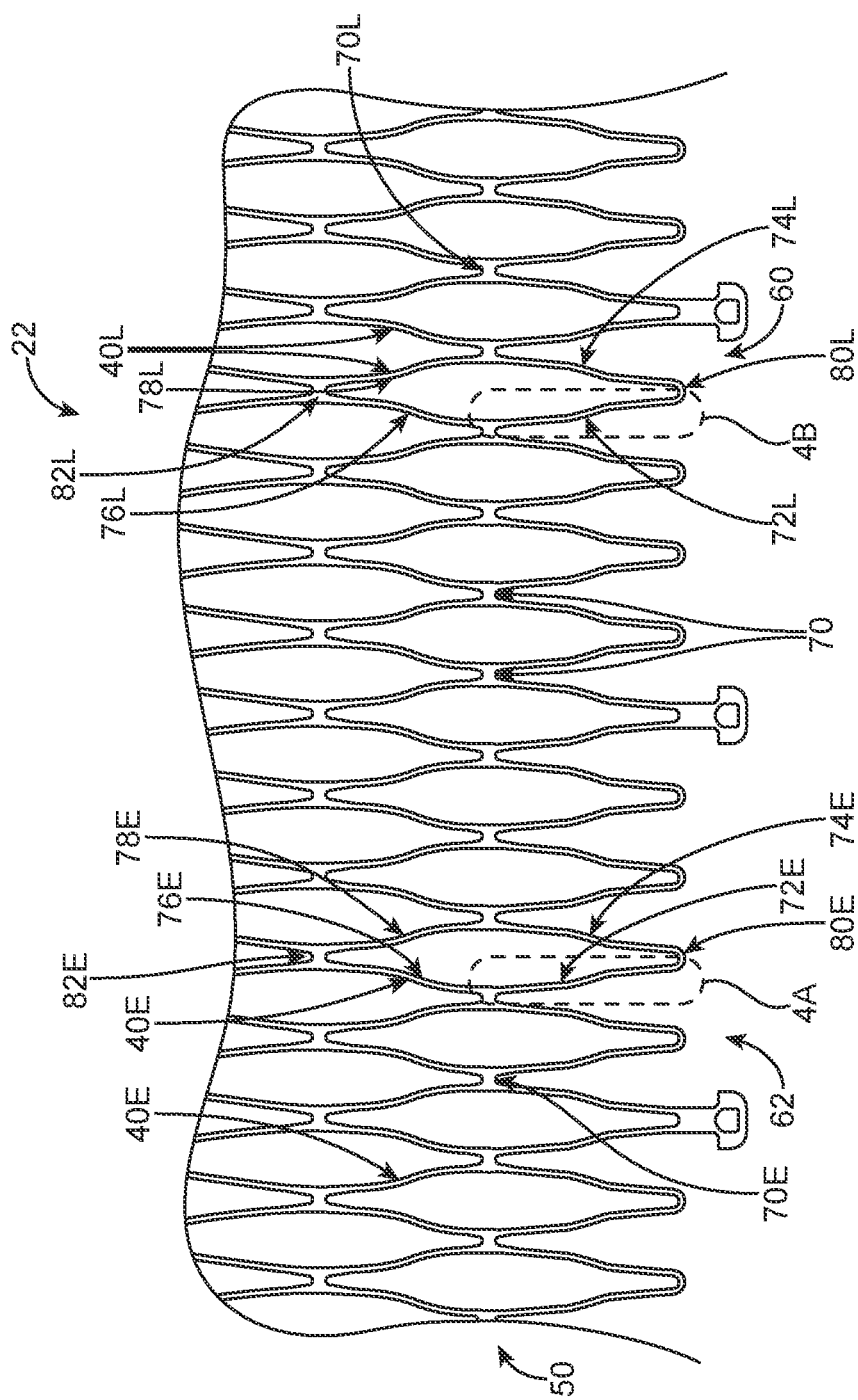
FIG. 3 is an enlarged, two-dimensional or unwrapped representation of a portion of the stent frame of FIG. 2A.

In some embodiments, the low radial stiffness first region 60 is generated by altering or reducing, but not eliminating, a geometric attribute of one or more of the structures otherwise generating one or more of the closed cells 40 and/or connections between the closed cells 40 of the first region 60. For example, FIG. 3 illustrates a portion of the stent frame 22 in a two-dimensional or "unwrapped" form (and in the compressed condition). For ease of explanation, the closed cells 40, and corresponding components thereof, of the low radial stiffness first region 50 are identified with the suffix "L" (e.g., the closed cells 40L), whereas the suffix "E" is utilized with structures of the second region 62 (e.g., the closed cells 40E). Each of the closed cells 40 of the first band 50 are connected to one another by a connector 70. Further, each of the closed cells 40 is formed or defined by a plurality of struts 72-78. For example, the closed cells 40E of the elevated stiffness second region 62 are each defined by struts 72E-78E. The first and second struts 72E, 74E are interconnected at a first node 80E, and the third and fourth struts 76E, 78E are interconnected at a second node 82E. A size and shape of each of the struts 72E-78E of the elevated stiffness closed cells 40E are identical or substantially identical (e.g., within 5% of a truly identical construction). The connectors 70 along the elevated radial stiffness second region 62 are also identical or substantially identical. While the closed cells 40L of the low stiffness first region 60 are each defined by struts 72L-78L interconnected by nodes 80L, 82L and are thus generally similar to the elevated stiffness cells 40E, at least one of the components 72L-78L, 80L, 82L, is not identical to the corresponding component 72E-78E, 80E, 82E of the elevated radial stiffness cells 40E. The low radial stiffness along the first region 60 is effectuated by altering a geometry of one or more of the struts 72L-78L and/or nodes 80L, 82L of one or more of the cells 40L, and/or one or more of the connectors 70L, along the first region 60.

Figure 4B:
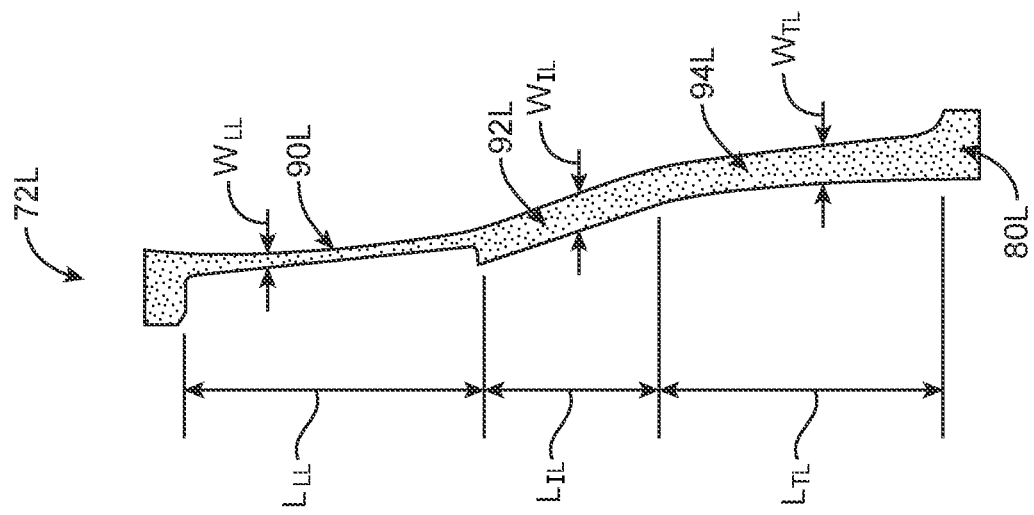
FIG. 4B is an enlarged side view of a strut component of another closed cell of the stent frame of FIG. 3, taken along the line 4B.
Figure 4A:
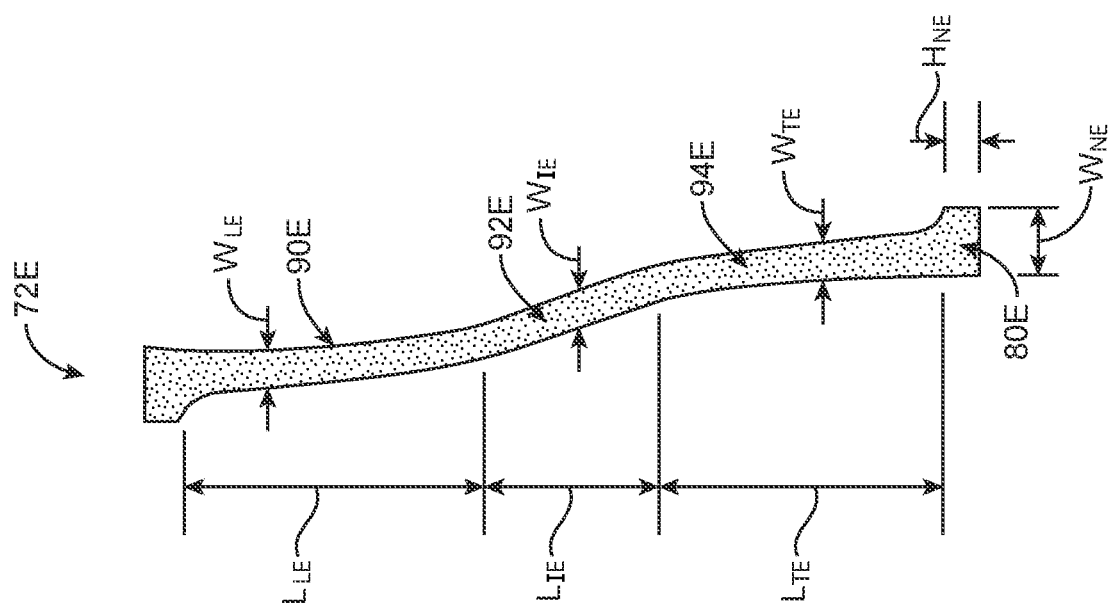
FIG. 4A is an enlarged side view of a strut component of a closed cell of the stent frame of FIG. 3, taken along the line 4A.

For example, FIG. 4A illustrates one of the struts 72E of one of the elevated radial stiffness closed cells 40E (FIG. 3). The strut 72E can be viewed as having or defining a leading segment 90E, an intermediate segment 92E, and a trailing segment 94E. The leading segment 90E defines a length $L_{LE}$ and a width $W_{LE}$. The intermediate segment 92E similarly defines a length $L_{IE}$ and a width $W_{IE}$. The trailing segment 94E has a length LTE and a width $W_{TE}$. The leading segment 90E extends from a connector 70E (partially illustrated in FIG. 3B), and can taper in width $W_{LE}$ to the intermediate segment 92E. The width $W_{IE}$ of the intermediate segment 92E can be substantially uniform in extension from the leading segment 90E to the trailing segment 94E. The trailing segment 94E can have an increasing width $W_{TE}$ in extension from the intermediate segment 92E to the corresponding node 80E (shown in partially in FIG. 4A). Finally, the node 80E has a height $H_{NE}$ and a width $W_{NE}$.

With the above geometric attributes of the strut 72E (or "elevated stiffness strut") in mind, FIG. 4B illustrates one non-limiting example of a strut 72L (or "low stiffness strut") of one of the low radial stiffness closed cells 40L in accordance with principles of the present disclosure. As a point of reference, the low stiffness strut 72L spatially corresponds with the elevated stiffness strut 72E of FIG. 4A (i.e., the struts 72E, 72L are both at the lower left quadrant of the corresponding closed cell 40E, 40L in FIG. 3). The low stiffness strut 72E has the same general shape and size as the elevated stiffness strut 72E, however a geometry of at least one of the segments 90L-94L differs from the corresponding segment 90E-94E of the elevated stiffness strut 72E. For example, the width $W_{LL}$ of the leading segment 90L is less than the corresponding leading segment width $W_{LE}$ of the elevated stiffness strut 72E. The reduction in mass reduces the radial stiffness of the low stiffness strut 72L (as compared to the radial stiffness associated with the elevated stiffness strut 72E). As a point of reference, the reduction in the width $W_{LL}$ is exaggerated in FIG. 4B for ease of understanding. In actual practice, the leading segment width $W_{LL}$ need only be slightly less than the normal width $W_{LE}$. In other embodiments, the width $W_{IL}$ of the low stiffness strut intermediate segment 92E can be less than the corresponding intermediate segment width $W_{IE}$ of the elevated stiffness strut 72E. Alternatively or in addition, the width $W_{TL}$ of the trailing segment 94L of the low stiffness strut 72L can be less than the width $W_{TE}$ of the trailing segment 94E of the elevated stiffness strut 72E.

Figure 4D:
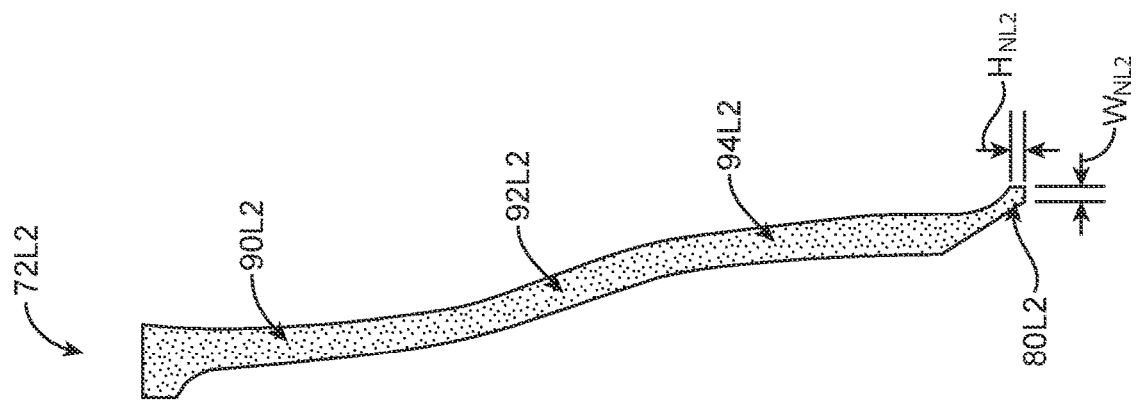
FIG. 4D is an enlarged side view of another strut component useful with the stent frame of FIG. 3.
Figure 4C:
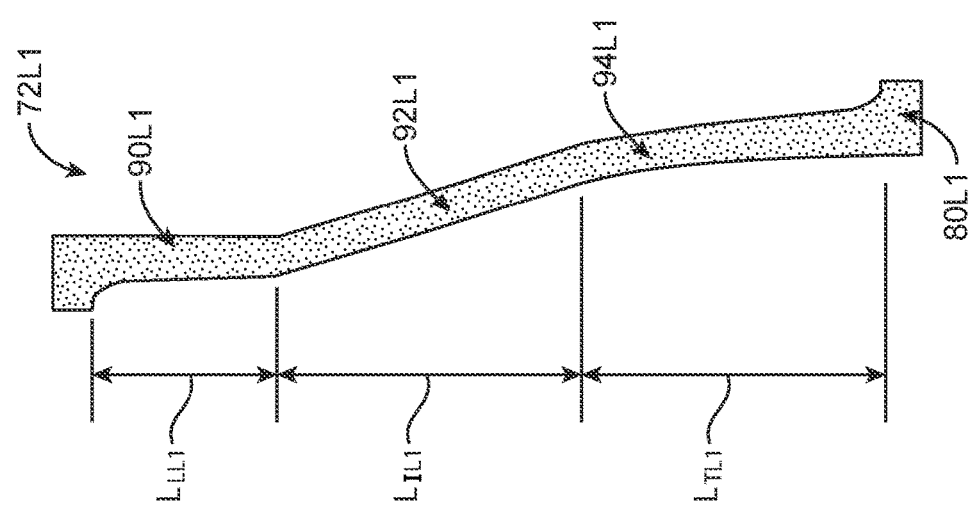
FIG. 4C is an enlarged side view of another strut component useful with the stent frame of FIG. 3.

Another non-limiting embodiment of a low stiffness strut 72L1 in accordance with principles of the present disclosure is shown in FIG. 4C. A comparison with the elevated stiffness strut 72E of FIG. 4A reveals that the length $L_{LL1}$ of the leading segment 90L1 is less than the length $L_{LE}$ of the leading segment 90E of the elevated stiffness strut 72E, whereas the length $L_{IL1}$ of the intermediate segment 92L1 is greater than the length LF of the elevated stiffness strut 72E (such that an overall length of the low stiffness strut 72L1 is the same as the overall length of the elevated stiffness strut 72E). The overall reduction in mass lessons the radial stiffness of the low stiffness strut 72L1 (as compared to the radial stiffness presented by the elevated stiffness strut 72E). Alternatively or in addition, the length $L_{IL1}$ of the intermediate segment 92L1 can be less than that associated with the elevated stiffness strut 72E, and the length $L_{TL1}$ of the low stiffness strut trailing segment 94L1 can be less or greater than that of the elevated stiffness strut 72E.

In yet other embodiments, the low stiffness struts of the present disclosure can incorporate both reduced width(s) and length(s). Moreover, and returning to FIG. 3, one, two, or all of the struts 72L-78L of the low radial stiffness cell(s) 40L can incorporate any of the geometric reductions described above in comparison to the counterpart strut 72E-78E of the elevated stiffness cells 40E.

FIG. 4D illustrates another embodiment low stiffness strut 72L2 in accordance with principles of the present disclosure and that again generally corresponds with the elevated stiffness strut 72E of FIG. 4A. A comparison of FIGS. 4A and 4D reveals that the node 80L2 of the low stiffness strut 72L2 has a reduced height $H_{NL2}$ and width $W_{NL2}$ as compared to the height $H_{NE}$ and width $W_{NE}$ of the elevated stiffness strut 72E. Alternatively, only one of the height $H_{NL2}$ or width $W_{NL2}$ can be reduced. Regardless, the reduction in mass of the node 80L2 effectuates a reduced radial stiffness (as compared to radial stiffness provided by the elevated stiffness strut 72E).

Returning to FIG. 3, in yet other embodiments, the reduced radial stiffness of the first region 60 can be accomplished by forming the connector 70L to have a size less than that associated with the connector 70E of the elevated stiffness second region 62.

The low radial stiffness first region 60 can be generated by a combination of any of the features described above. That is to say, while the closed cells 40L and the connectors 70L of the low radial stiffness first region 60 are generally similar to the closed cells 40E and the connectors 70E of the elevated stiffness second region 62, the reduced radial stiffness is achieved by altering (e.g., reducing) one or more of the strut lengths, widths, node height, node width, degree of taper, and/or connector dimensions. Further, the illustrated size and shape of the elevated stiffness strut 72E, as well as the overall construction of the elevated radial stiffness cells 40E is but one acceptable configuration encompassed by the pending disclosure. A plethora of different strut and/or closed cell shapes, sizes, and patterns are equally acceptable so long as at least one closed cell of the low radial stiffness region 60 incorporates a geometric reduction as compared to the closed cells of the elevated radial stiffness region 62. With embodiments in which more than one band of the stent frame 22 incorporates the varying radial stiffness features (e.g., the first and second bands 50, 52 of FIG. 2A), the low radial stiffness region 60 of longitudinally consecutive bands are aligned and in some embodiments can be similarly constructed. For example, FIG. 2 illustrates the first and second bands 50, 52 as each having the low radial stiffness region 60 (i.e., the low radial stiffness region 60 of the stent frame 22 is optionally collectively defined by struts of two (or more) of the bands 50, 52).

Returning to FIG. 2A, the low radial stiffness region 60 can be located at any longitudinal point along the stent frame 22. In general terms, the low radial stiffness region 60 is arranged at a location corresponding with expected cardiac conductive pathways of the native valve anatomy upon implant. For example, the stent frame 22 of FIG. 2A is configured for implantation at the aortic valve. As described below, conductive pathways are likely to be found along the inflow end 32. Thus, the low radial stiffness region 60 is provided at an anatomic location corresponding with the inflow end 32. Alternatively, the low radial stiffness region 60 can be located anywhere along the stent frame 22, for example at the outflow end 36, or longitudinally between the inflow and outflow ends 32, 36.

Figure 5A:
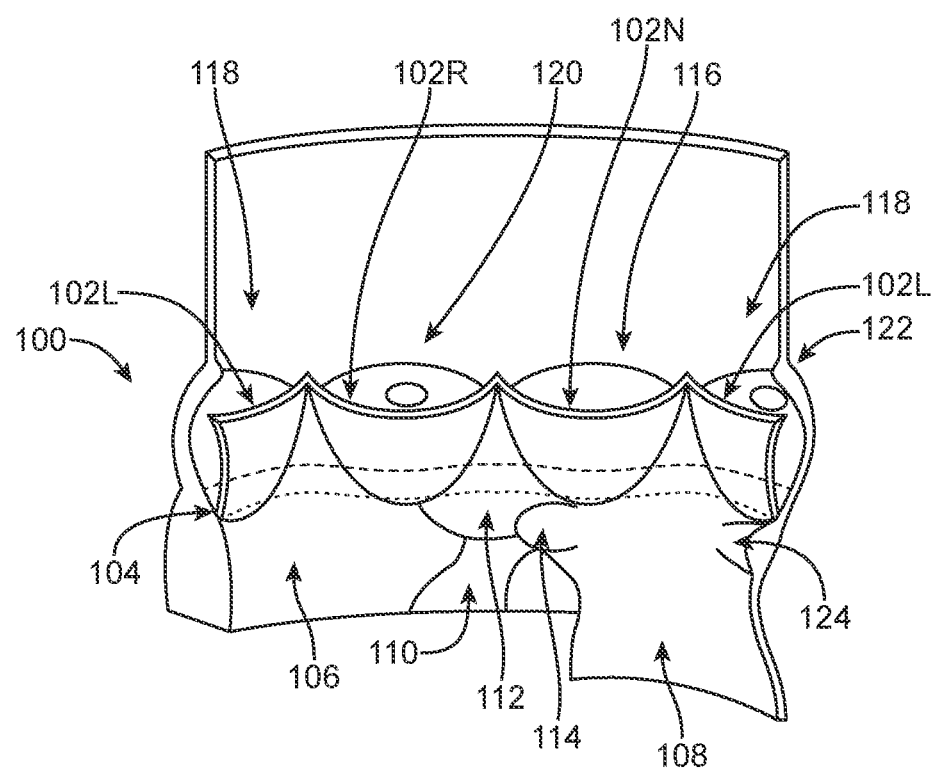
FIG. 5A is a cross-sectional, dissected illustration of an aortic valve and surrounding anatomy.

With embodiments in which the prosthetic heart valve 20 is intended to be implanted at the aortic valve, certain conductive pathways or fibers naturally occur at the aortic valve and surrounding anatomy. For example, FIG. 5A illustrates the anatomy of an aortic valve and surrounding structures 100 as found in the normal heart. Three valvular leaflets 102L, 102R. 102N are attached across a ventriculoarterial junction 104 in a crown-like fashion running onto either a muscle of the ventricular septum 106 or the mitral valve 108. A left bundle branch 110 emerges at a junction of a membranous septum 112 and right fibrous trigone 114 at the base of the interleaflet triangle between the right and noncoronary leaflets 102R. 102N. The left bundle branch 110 is separated from the aortic valve leaflets 102L. 102R. 102N by the interleaflet triangle. A noncoronary sinus 116, left coronary sinus 118, right coronary sinus 120, sinutubular junction 122, and left fibrous trigone 124 are also identified.

Figure 5B:
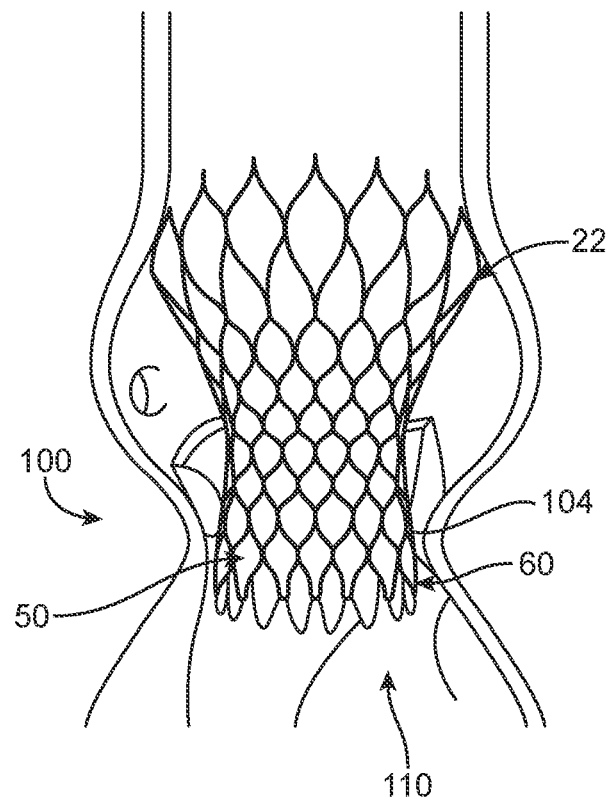
FIG. 5B illustrates the prosthetic heart valve of FIG. 1A implanted to the aortic valve of FIG. 5A.
Figure 5C:
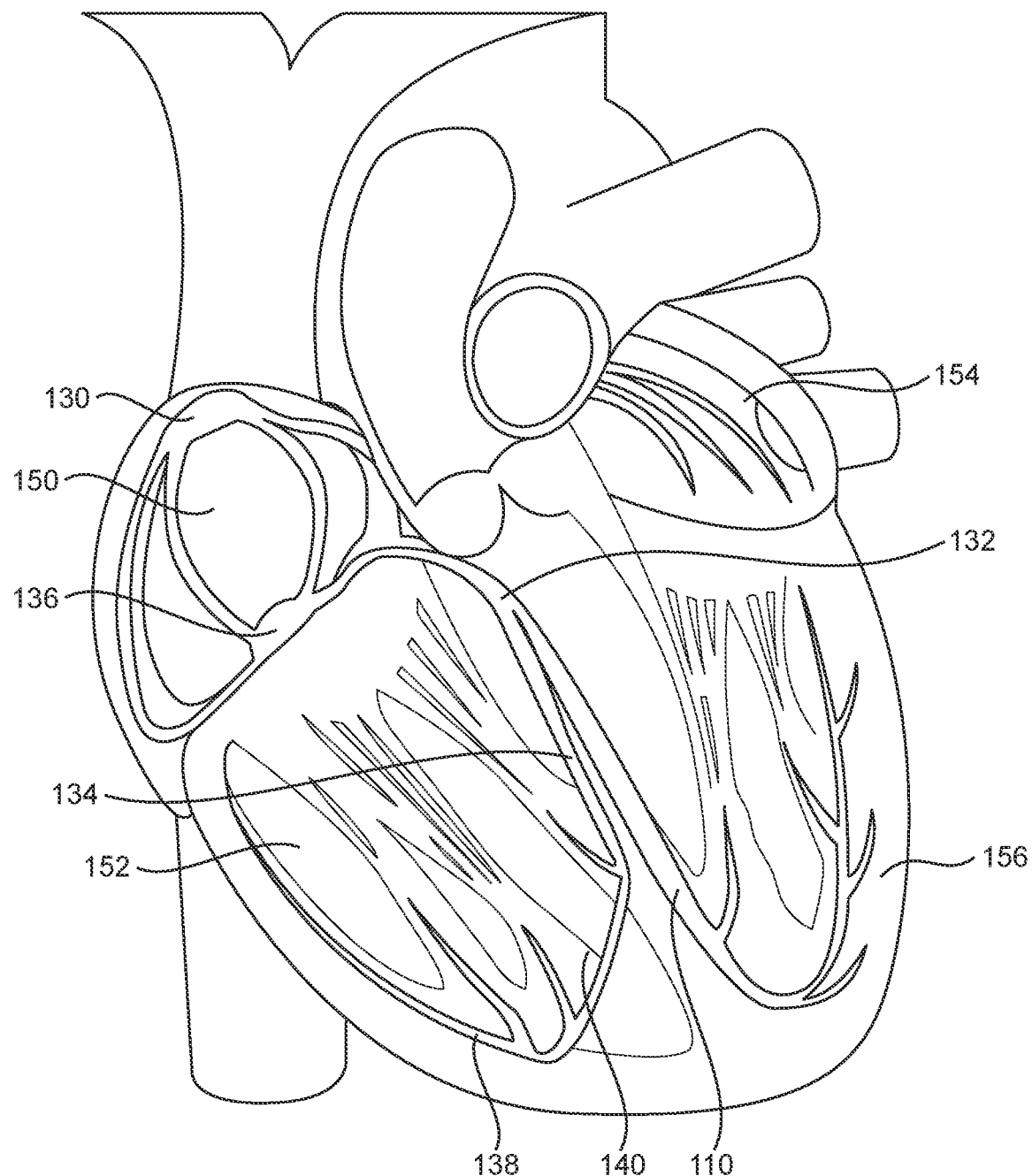
FIG. 5C is a cross-sectional view of the human heart and identifies various conductive pathways.

FIG. 5B illustrates the stent frame 22 implanted to the aortic valve 100. The stent frame 22 crosses the ventriculoarterial junction 104 and lies over a region of the left bundle branch 110. In this regard, the low radial stiffness first region 60 is aligned with the left bundle branch 110. As a result, the force exerted by the stent frame 22 on the left bundle branch 110 is reduced (as compared to a conventional configuration in which the band 50 would have a uniform, elevated radial stiffness along the entire circumference and thus apply a high force on to the left bundle branch 110), and is thus less likely to negatively impact the conductive pathways of the heart. In more general terms, depending upon the native valve being repaired, the localized low radial stiffness region 60 is aligned with an expected location of native conduction fibers, several examples of which are identified in FIG. 5C and include the left bundle branch 110, SA node 130, Bundle HIS 132, right bundle branch 134, AV node 136, Purkingee fibers 138. Moderator band 140, and other locations on the conductive pathways of the heart while providing necessary radial resistive force and fatigue strength to maintain long term fixation across the valve being replaced. As a point of reference, the right atrium 150, right ventricle 152, left atrium 154, and left ventricle 156 are also identified in FIG. 5C.

Figure 6:
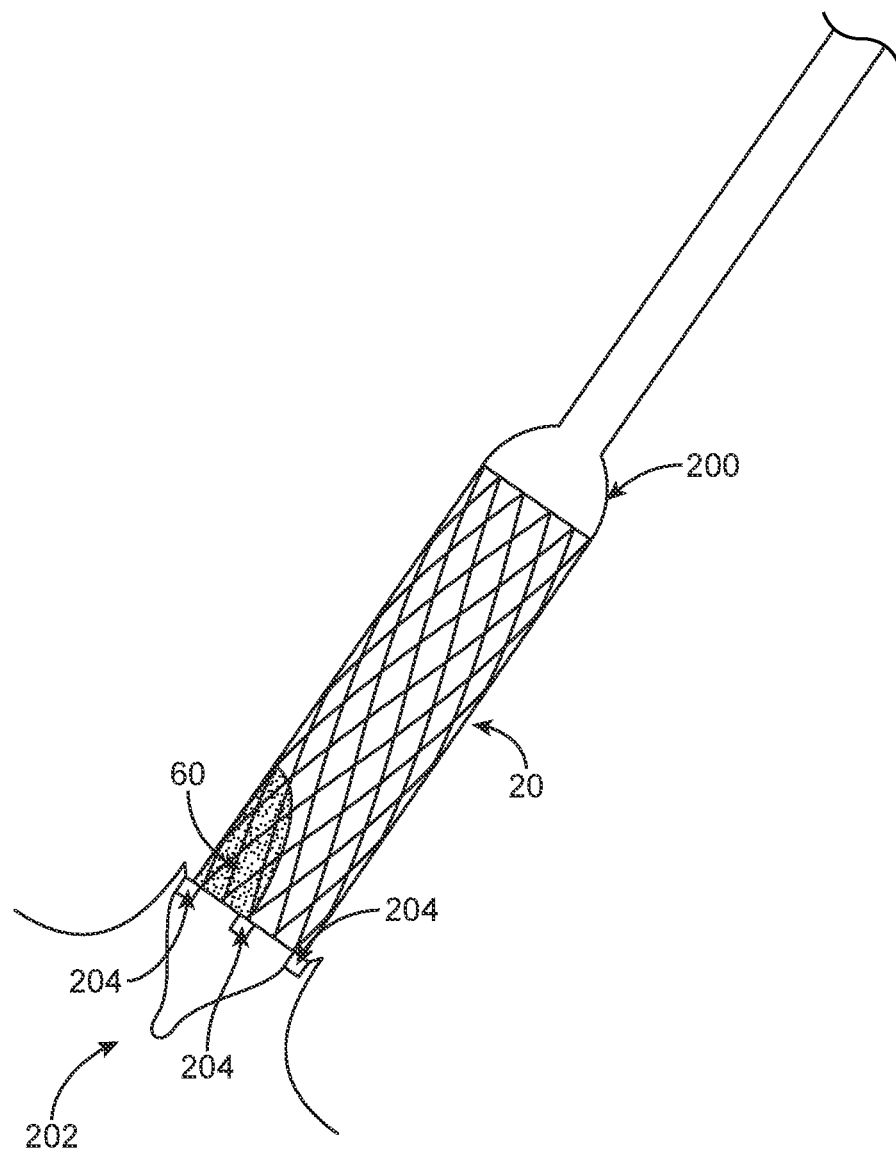
FIG. 6 illustrates, in simplified form, delivery and alignment of the prosthetic heart valve of FIG. 1A to a native valve.

The stented transcatheter prosthetic heart valves of the present disclosure can be delivered to the targeted heart valve in a variety of manners using various transluminal delivery tools as known in the art. In general terms, and with reference to FIG. 6, the prosthetic heart valve 20 is compressed and held within an outer delivery sheath or capsule 200 (referenced generally) and advanced in this compressed condition toward a target site 202. Before deploying the prosthesis 20 (e.g., by retracting the capsule 200 from over the compressed prosthesis 20), the prosthesis 20 is optionally spatially oriented to arrange or align the low radial stiffness region 60 (identified generally with stippling in FIG. 6) with targeted tissue (i.e., where native conductive fibers are expected to reside). In this regard, the stented prosthetic heart valve 20 and/or the capsule 200 can include or carry markers 204 (e.g., radiopaque markers) that correspond with the commissure points 38 (FIG. 1B) of the prosthesis 20. The low radial stiffness region 60 has a known circumferential location relative to the commissure points 38 and thus relative to the markers 204. With an aortic procedure, the markers 204 can then be aligned (e.g., fluoroscopic) with the native commissures between the native noncoronary and right coronary cusps; with this spatial arrangement, the deployed prosthesis 20 will naturally locate the low radial stiffness region 60 over the conductive fibers of the left bundle branch. A variety of other delivery and optional alignment techniques are also envisioned.

Although the present disclosure has been described with reference to preferred embodiments, workers skilled in the art will recognize that changes can be made in form and detail without departing from the spirit and scope of the present disclosure.

What is claimed is:

1. A method of treating a native heart valve of a patient, the method comprising:
    delivering a prosthetic heart valve to the native heart valve with a delivery device, the prosthetic heart valve including a stent frame maintaining a valve structure, the stent frame configured to expand from a compressed condition to a natural, expanded condition, the stent frame comprising a lattice structure defining at least a first band of closed cells extending about an entirety of a circumference of the stent frame, wherein the first band defines a first region and a second region and is configured to have a variable radial stiffness along the circumference in the natural, expanded condition;
    at least partially deploying the prosthetic heart valve from the delivery device into the native heart valve, including the stent frame self-expanding toward the natural, expanded condition; and aligning the first region with a conductive pathway of the native heart valve.

2. The method of claim 1, wherein the first region comprises a maximum radial stiffness less than a minimum radial stiffness of the second region.

3. The method of claim 1, wherein aligning includes aligning a radiopaque marker of the stent frame with a native commissure of the native heart valve.

4. The method of claim 1, wherein the conductive pathway is one of conduction fibers of a left ventricular septum, SA node, and bundle of His.

5. The method of claim 1, wherein each of the closed cells of the first band are uniformly spaced along the circumference.

6. The method of claim 1, wherein the valve structure includes a plurality of leaflets arranged to define an inflow side and an outflow side, and further wherein the first band is located proximate the inflow side.

7. The method of claim 1, wherein an arc angle of the first region is less than an arc angle of the second region.

8. The method of claim 1, wherein each of the closed cells includes a plurality of interconnected struts, and further wherein a geometry of at least one of the struts of the closed cells of the first region is less than a corresponding geometry of a corresponding strut of the closed cells of the second region.

9. The method of claim 8, wherein the geometry is at least one of a length and a width of a segment of the strut.

10. The method of claim 8, wherein at least one of the struts at the first region is tapered resulting in a variance in mass of the tapered strut as compared to struts at the second region.

11. The method of claim 1, wherein the first band further includes a joint connector connecting immediately circumferentially adjacent ones of the closed cells to one another, and further wherein a geometry of each of the joint connectors of the first region is less than a corresponding geometry of each of the joint connectors of the second region.

12. The method of claim 1, wherein the closed cells are arranged to further define a second band of closed cells extending about an entirety of the circumference, the second band being immediately longitudinally adjacent the first band, and further wherein the second band is configured to have a variable radial stiffness along the circumference in the natural, expanded condition.

13. The method of claim 12, wherein the first and second bands collectively define a low radial stiffness region.

14. The method of claim 1, wherein the closed cells are formed by struts and interconnected with nodes extending between adjacent cells, and further wherein the nodes of the first band are configured to have a variance in mass to result in a variable radial stiffness along the circumference in the natural, expanded condition.

15. A method of treating a native heart valve of a patient, the method comprising:
  delivering a prosthetic heart valve to the native heart valve with a delivery device, the prosthetic heart valve including a stent frame maintaining a valve structure, the stent frame configured to expand from a compressed condition to a natural, expanded condition, the stent frame comprising a lattice structure defining at least a first band of closed cells extending about an entirety of a circumference of the stent frame, wherein the first band is configured to have a variable stiffness along the circumference in the natural, expanded condition, the stent frame further including a radiopaque marker;
  at least partially deploying the prosthetic heart valve from the delivery device into the native heart valve, including the stent frame self-expanding toward the natural, expanded condition; and
  aligning the radiopaque marker with a desired anatomical location of the native heart valve.

16. The method of claim 15, wherein the radiopaque marker is aligned with a commissure of the native heart valve.

17. The method of claim 15, wherein each of the closed cells of the first band are uniformly spaced along the circumference.

\* \* \* \* \*